US007015244B1

(12) United States Patent
Zamoyski

(10) Patent No.: US 7,015,244 B1
(45) Date of Patent: Mar. 21, 2006

(54) INHALABLE CHEMICAL DEBRIDEMENT FOR COPD

(76) Inventor: Mark Zamoyski, 988 Foothill Dr., San Jose, CA (US) 95123

(*) Notice: Subject to any disclaimer, the term of this patent is extended or adjusted under 35 U.S.C. 154(b) by 180 days.

(21) Appl. No.: 10/696,863

(22) Filed: Oct. 30, 2003

Related U.S. Application Data

(60) Division of application No. 09/928,981, filed on Aug. 13, 2001, now abandoned, which is a continuation-in-part of application No. 09/132,153, filed on Aug. 11, 1998, now abandoned.

(51) Int. Cl.
*A61I 31/35* (2006.01)
*A61K 31/335* (2006.01)

(52) U.S. Cl. ...................... 514/453; 449/451; 449/450; 449/452; 449/456; 449/460; 449/475

(58) Field of Classification Search ..................... None
See application file for complete search history.

(56) References Cited

U.S. PATENT DOCUMENTS

| | | | |
|---|---|---|---|
| 4,744,981 | A | 5/1988 | Pavanasasivam |
| 4,906,452 | A | 3/1990 | Sivam |
| 6,342,520 | B1 | 1/2002 | Zamoyski |
| 6,346,251 | B1 | 2/2002 | Zamoyski |
| 6,355,251 | B1 | 3/2002 | Zamoyski |
| 6,559,178 | B1 | 5/2003 | Zamoyski |

OTHER PUBLICATIONS

REGISTRY, "trichothecene," Jun. 23, 2005.*
Okazaki et. al., "Antiviral Activity of Macrocyclic Trichothecene Mycotoxins . . . " Agricultural and Biological Chemistry, 1989, vol. 53 pp. 1441-1443.
Okazaki et. al., "Inhibition by Trichothecene Mycotoxins of Replication of Herpes Simplex Virus Type 2", Agricultural and Biological Chemistry, 1988, vol. 52 pp. 795-801.

Dearborn et. al., Morbidity and Mortality Weekly Report, Dec. 9, 1994, vol. 43, No. 48, pp. 881-883.

NIEHS press release, NIEHS, CDC Fund Study of Fungus Fatal to Cleveland Infants, Jul. 30, 1997. 1 Page.

U. S. AMRIID, "Understanding the Threat", website printout on Aug. 27, 1999, 7 pages.

Fauci et. al., Harrison's Principles of Internal Medicine, 14th edition, McGraw Hill, 1998 , pp. 528.

Alberts, et. al. Molecular Biology of the Cell, Third edition, Garland Publishing, pp. 896-897, (1994).

* cited by examiner

*Primary Examiner*—Rebecca Cook

(57) ABSTRACT

Sesquiterpene epoxide compounds (trichothecenes) and methods for administering such compounds by inhalation for chemical debridement of cells in the lungs of COPD patients are disclosed.

5 Claims, 5 Drawing Sheets

INHALABLE CHEMICAL DEBRIDEMENT FOR COPD

CROSS REFERENCE TO RELATED APPLICATIONS

This application is a divisional of application Ser. No. 09/928,981 filed Aug. 13, 2001 which is a CIP of application Ser. No. 09/132,153 filed Aug. 11, 1998, abandoned.

In present invention applicant teaches use of inhalation of trichothecenes in locally cytotoxic and toxic doses as a chemo debridement treatment option non malignant, hyperproliferative cell populations in conditions such as COPD.

As such, present application is related to several other patents and applications filed by applicant. In U.S. Pat. No. 6,355,251 issued on Mar. 12, 2002 for epidermal chemexfoliation applicant uses topical application of locally toxic doses to kill off a desired percentage of epidermal cells. In U.S. Pat. No. 6,559,178 issued on May 6, 2003, applicant disclosed use of injectable, locally toxic doses for non malignant conditions such as BPH and endometriosis. U.S. Pat. No. 6,342,520 issued on Jan. 29, 2002 employed cytotoxic doses to provide a locally injectable chemotherapeutic. U.S. Pat. No. 6,346,251 issued on Feb. 12, 2002 employed topical application and inhibitory doses to exert locally immunosuppressive affects as well dismantle the cell cycle control system of both psoriatic and endothelial cells as a treatment for psoriasis.

STATEMENT REGARDING FEDERALLY SPONSORED RESEARCH

Not Applicable.

INCORPORATION-BY-REFERENCE OF MATERIAL SUBMITTED ON A CD

Not Applicable

BACKGROUND OF THE INVENTION—FIELD OF THE INVENTION

Prior art's use of trichothecene has been limited to cytotoxic doses for treating cancer and dates back to the early 1980s. Anguidine, a simple trichothecene, was administered in cytotoxic doses, however its use was abandoned after Phase II results showed overall tumor response rate was low and there was considerable hematologic toxicity. U.S. Pat. Nos. 4,744,981 and 4,906,452 embody the direction prior art took to solve the systemic toxicity problem caused by trichothecene's lack of specificity in cellular internalization and blood insolubility; they proposed using conjugates of trichothecene with monoclonal or polyclonal antibodies to selectively deliver the toxin to tumors and proposed glycosylation of trichothecenes to increase blood solubility. Applicant took an exactly opposite approach to prior art and demonstrated how certain trichothecenes could be used unconjugated and unglycosylated to treat tumors by reversing the direction of administration from tissue to blood (interstitial perfusion), dispersing the trichothecenes between the intercellular spaces and then using the gap junction transport system to cleanly localize the trichothecene in the tumor, for which applicant was granted U.S. Pat. No. 6,342,520.

In the present invention, applicant uses inhalation to achieve the novel tissue side administration method, without inducing systemic toxicity. Applicant has also extended the utility of trichothecenes by employing both cytotoxic and toxic dose levels to provide a novel method of chemical debridement of over proliferated lung tissue.

BRIEF SUMMARY OF THE INVENTION

The current invention proposes administration, by inhalation, of locally cytotoxic and toxic doses of certain sesquiterpene epoxides (trichothecenes) to provide a method of chemical debridement of diseased or overproliferation cells in the lungs of Chronic Obstructive Pulmonary Disease (COPD) patients. Present invention will provide methods of chemical debridement of over proliferated lung cells in COPD patients versus prior art's surgical procedures.

BRIEF DESCRIPTION OF DRAWING FIGURES

Figures 1A, 1B:
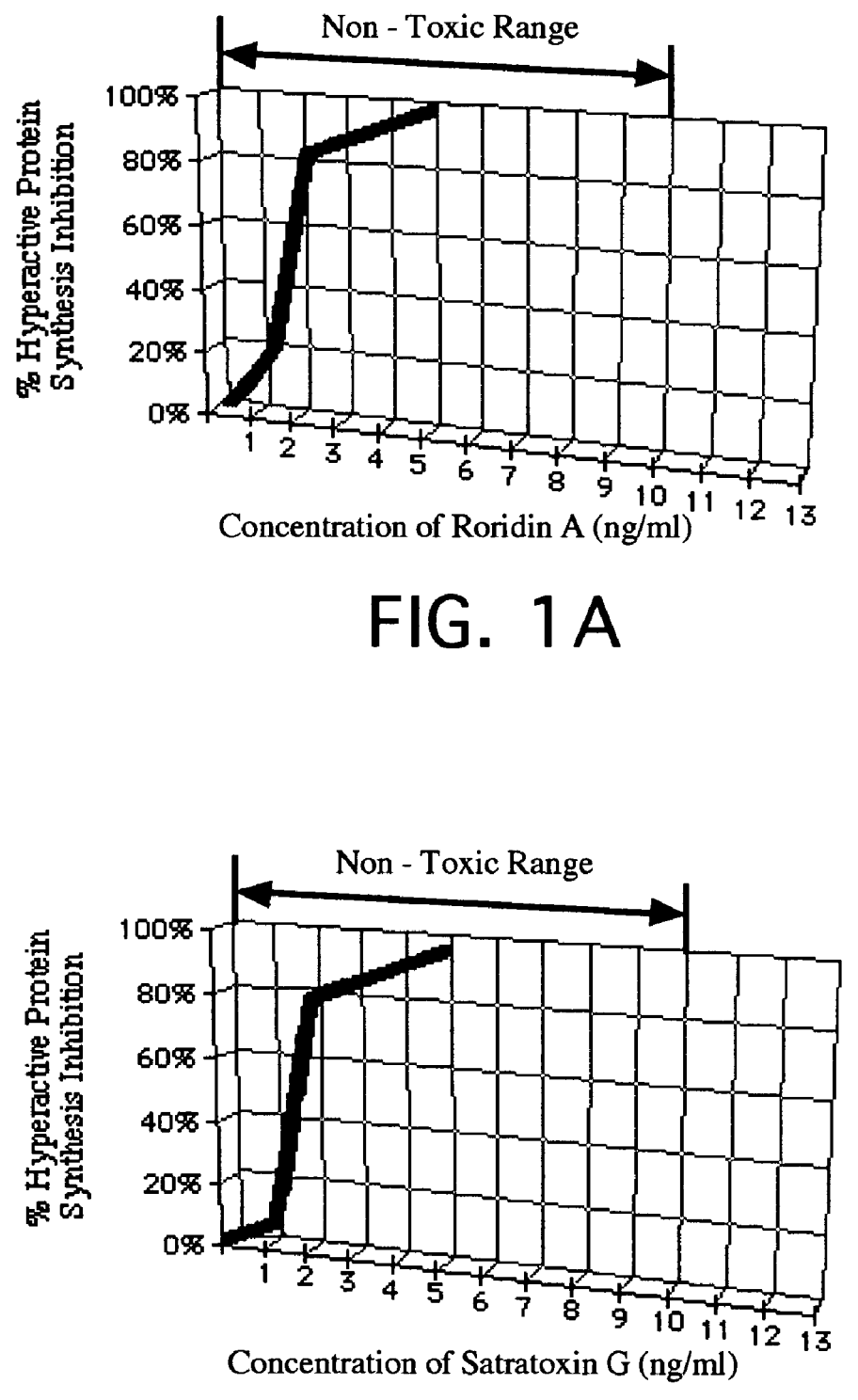

FIG. 1A shows the hyperactive protein synthesis inhibiting dose profile in human cells of Roridin A, a representative macrocyclic trichothecene.

FIG. 1B shows the hyperactive protein synthesis inhibiting dose profile in human cells of Satratoxin G, a representative macrocyclic trichothecene.

DETAILED DESCRIPTION OF THE INVENTION

The treatments disclosed below involve administration of biologically active trichothecenes by inhalation to kill over proliferated cell populations in the lungs and to inhibit the regrowth of cell populations in the lungs. Materials and methods for achieving this are described below.

Overview of Protein Synthesis Inhibition:

The most fundamental function a cell is protein synthesis (i.e. expression of its DNA). Proteins make up ~60% of a dry cell's mass by weight. In very broad and general terms, as cells mature and differentiate in the body, they reach an equilibrium in protein synthesis and protein degradation and settle down to perform their given function in this relative state of homeostasis. There are two notable exceptions that cause massive perturbations to this homeostasis: 1) when a cell is called upon to grow and divide and 2) when certain secretory cells are called upon to produce large amounts of proteins for secretion. Although the cell signaling signaling pathways, intracellular transduction pathways, and spectrum of protein(s) to be produced are quite different in growth versus secretion, normal growth and secretion events share one major similarity in their end result: massively accelerated protein synthesis. A cell that is called on to grow (cycling cell) has as much as 5 times the protein synthesis activity of a non cycling cell. Likewise, secretory cells such as those of the immune system become protein factories producing massive amounts of antibodies, mediators, growth factors, or other proteins when stimulated to do so.

There are also abnormal conditions such as cancer and viral infections that share the same property of hyperactive protein synthesis versus normal quiescent cells. Cancer is a growth and divide type event, and even though the signaling mechanism is different in that it is self-induced intracellularly by several genetic mutations, the end result is also hyperaccelerated protein synthesis characteristic of a cycling cell. Viruses invade a cell, parasitize the host cellular machinery, and convert the cell into a factory producing massive amounts of viral proteins, much like a secretory cell.

Figure 3:
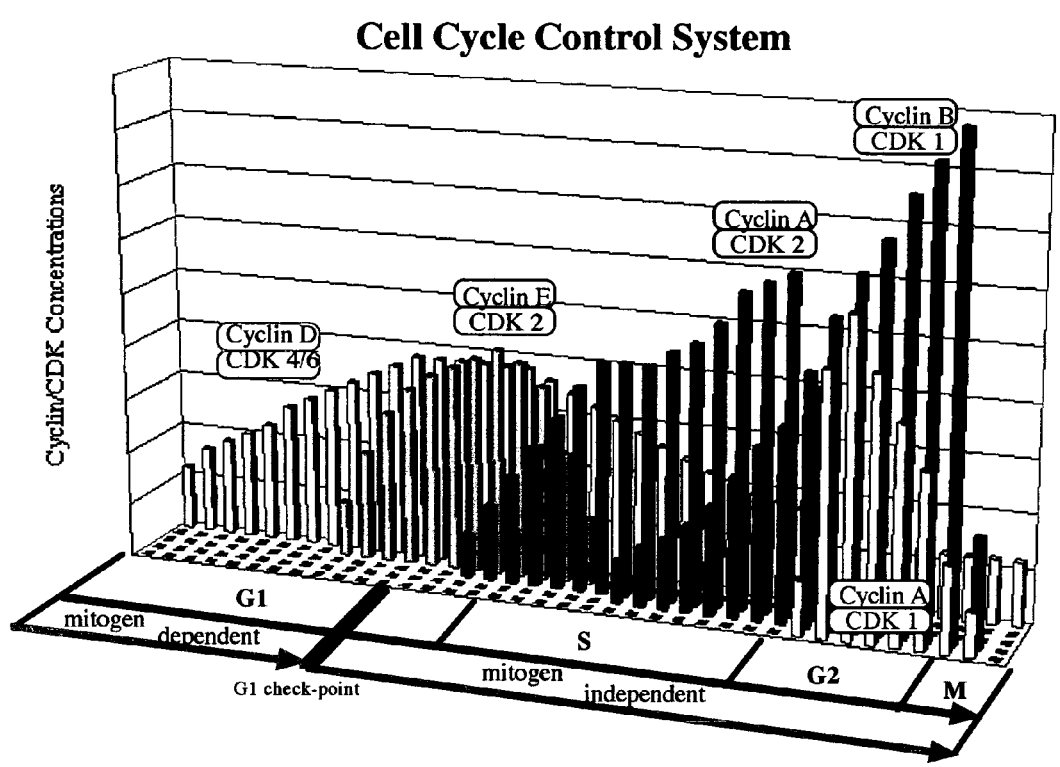
FIG. 3 shows the hyperactive Cyclin/CDK protein synthesis activity required at various points in the cell cycle to drive the cell through the cell cycle (i.e. the cell cycle control system).
Figure 4:
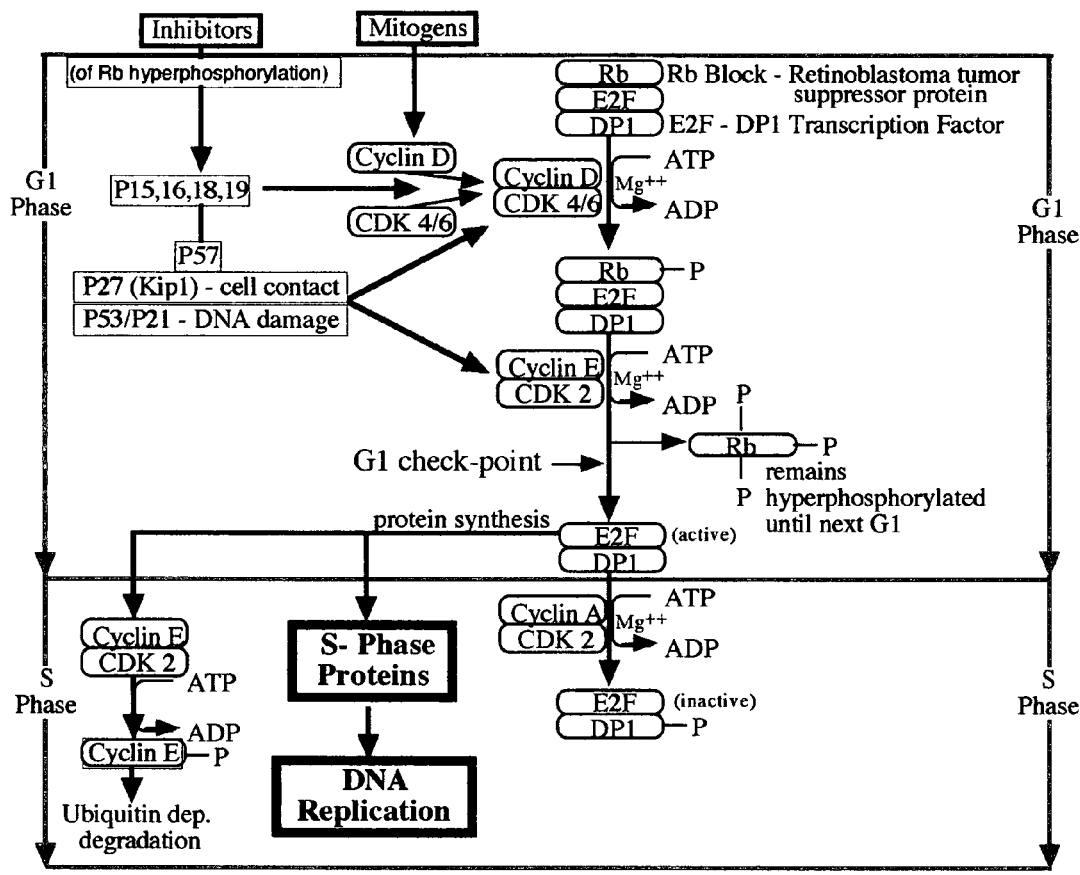
FIG. 4 shows the molecular pathways depending on the hyperactive protein synthesis of the G1 cyclin/CDK proteins required to drive the cell through the G1 phase of the cell cycle.

Inhibiting protein synthesis affects cells in a dose dependent manner and affects actively cycling cells differently than non cycling cells. Briefly inhibiting protein synthesis (MBOC 89-6897) stops cells from cycling by dismantling the cell cycle control system. At these low doses, protein synthesis inhibitors (PSIs) stop actively cycling cells from cycling by preventing the hyperactive Cyclin/CDK protein synthesis activity required to drive the the cell cycle control system as shown if FIG. 3 and FIG. 4 (hereinafter referred to as inhibitory or G zero inducing dose). Inhibitory doses also attenuate hyperaccelerated protein synthesis by secretory cells such as activated cells of the immune system.

At moderate doses PSIs exhibit toxicity to actively cycling cells (hereinafter referred to as the cytotoxic dose). Actively cycling cells have as much as 500% more protein synthesis activity than non cycling cells with critical hyperactive burst of protein synthesis required at various point in the cell cycle. Interference with protein synthesis has lethal consequences for actively cycling cells in various phases of the cell cycle. The cytotoxic mechanisms of action (MOAs) against actively cycling cells are disclosed by applicant in U.S. Pat. No. 6,342,520 for Locally Injectable Chemotherapeutics from column 4 line 29 to the end of column 7, and incorporated herein by reference. These MOAs include DNA fragmentation/damage from depolymerization of microtubules and improper chromatin formation from inhibited histone synthesis.

At high doses, PSIs exhibit toxicity to all cells (hereinafter referred to as the toxic dose).

Trichothecenes Defined:

Fungi of the genera *Fusarium, Myrotecium, Trichoderma, Stachybotrys* and others produce Trichothecene mycotoxins. Trichothecenes constitute a family of fungal sesquiterpene epoxides that inhibit protein synthesis. Trichothecene mycotoxins are low molecular weight (250–700 daltons), non volatile compounds, and of over 150 trichothecenes have been identified. There are two broad classes: those that have only a central sesquiterpenoid structure and those that have an additional macrocyclic ring (simple and macrocyclic trichothecenes, respectively).

As used in this application, "therapeutics", "biologically active agent", or "trichothecene" are defined as either simple or macrocyclic trichothecenes and include molecules of the following general chemical formulas: Simple trichothecenes are categorized into three groups with the following chemical formulas:

Group A:

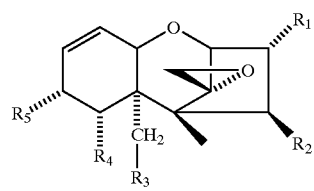

Wherein $R_1$ is H, OH, or

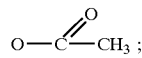

$R_2$ is H, OH, or

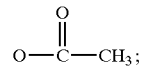

$R_3$ is H, OH, or O—C—CH$_3$;
$R_4$ is H or OH; and

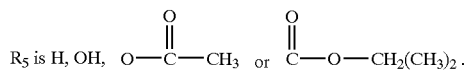

Group B:

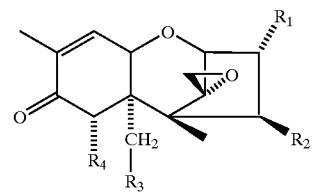

Wherein $R_1$ is H, OH, or

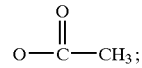

$R_2$ is H, OH, O—C(=O)—CH$_3$ or O—C(=O)—CH=CH—CH$_3$;

$R_3$ is H, OH, or $$O-\overset{O}{\underset{\|}{C}}-CH_3;$$

$R_4$ is H, OH, or $$O-\overset{O}{\underset{\|}{C}}-CH_3;$$

Group C:

Wherein R' is OH or $$O-\overset{O}{\underset{\|}{C}}-CH=CH-CH_3.$$

Macrocyclic Trichothecenes can be described by the following general chemical formulas:

Wherein $R_1$ is OH, or $$O\overset{O}{\underset{\|}{C}}-CH_3;$$

$R_2$ is H, OH, $O-\overset{O}{\underset{\|}{C}}-CH_3$ or $OCOCH_2CH(CH_3)_2$;

and R' is any molecule composed predominantly, or in its entirety, of combinations of C, H, and O:

Some representative examples of R' include:

Satratoxin H:

Satratoxin G:

or molecules of the following general formula:

Wherein $R_1$ is H, OH, or $$O-\overset{O}{\underset{\|}{C}}-CH_3;$$

$R_2$ is H, OH, $O-\overset{O}{\underset{\|}{C}}-CH_3$ or $OCOCH_2CH(CH_3)_2$;

and

R' is any molecule composed predominantly, or in its entirety, of combinations of C, H, and O.

A more comprehensive listing of trichothecenes is included in U.S. Pat. Nos. 4,744,981 and 4,906,452, incorporated herein by reference.

Trichothecenes are fast acting potent inhibitors of protein synthesis in eucaryotic cells. Their main effects are on rapidly proliferating tissues such as bone marrow, skin, mucosa epithelia, and germ cells. The sesquiterpenoid ring binds to ribosomes, inhibiting protein synthesis. The macrocyclic ring enhances cell binding and internalization.

Trichothecenes are invisible to the immune system since they neither contain nor produce amino acids. Since trichothecene molecules contain only carbon, hydrogen, and oxygen they are not subject to proteolytic degradation. U.S. Pat. No. 4,906,452 (column 11 first paragraph) further discloses that some studies of the rates at which certain trichothecenes are converted into biologically inactive molecules (apotrichothecenes) found that macrocyclic trichothecenes are inactivated quite slowly and only by intracellular acid catalysis as might occur in lyzosomes.

Trichothecenes are extremely stable to heat and ultraviolet light inactivation. Heating to 500° F. for 30 minutes is required for inactivation. Brief exposure to NaOH destroys toxic activity. These substances are relatively insoluble in water but are highly soluble in ethanol, methanol, and propylene glycol.

Figure 5A:
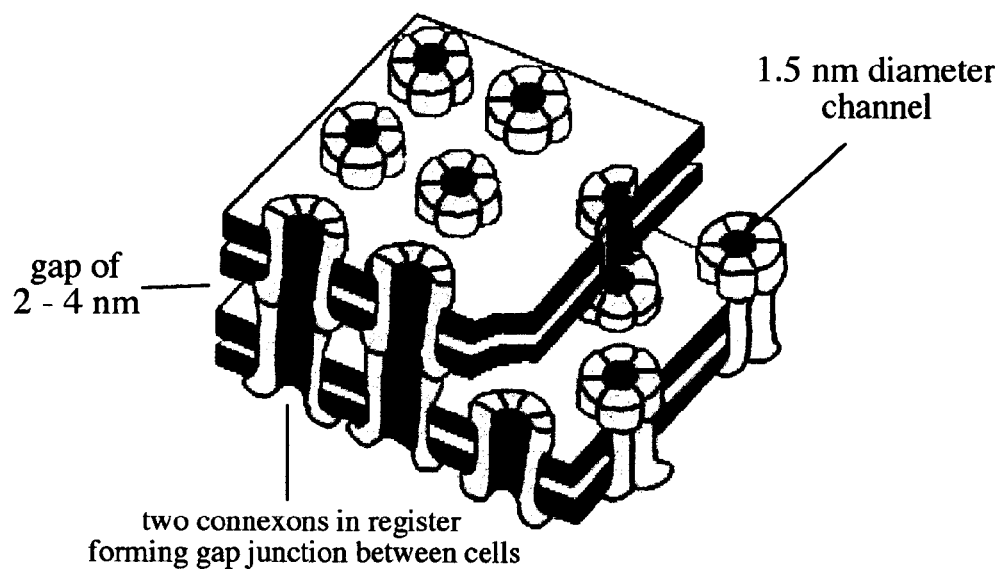
FIG. 5A shows a cross section of the spacing between two adjacent cell as well as the related structures referred to as gap junctions that connect adjoining cells.
Figure 5B:
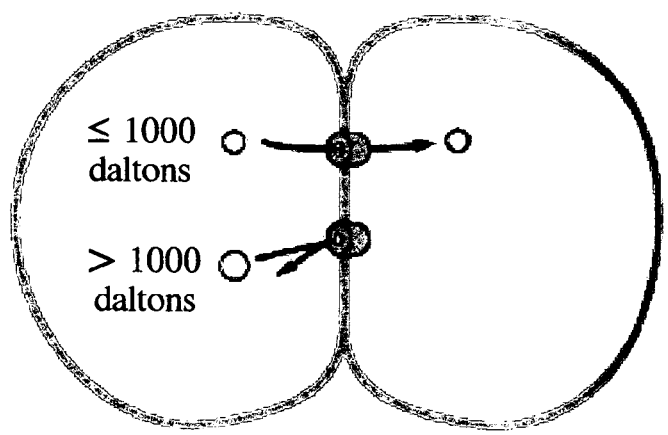
FIG. 5B shows the particle size limitation for gap junction transport between two adjacent cells.

Internalization and Localization Attributes:

The novelty and unobviousness of applicant's proposal stems in part from several attributes of trichothecene that are not generally known to prior art. Certain trichothecenes are capable of rapid cellular internalization with extreme reluctance to enter the blood stream as well as being capable of gap junction transport and having extremely slow intracellular inactivation times. Cells of an organ or tissue type are spaced 2–4 nm apart as shown if FIG. 5A and connexons in the bi-lipid cell membrane connect adjacent cells metabolically by what are referred to as gap junctions. Gap junctions allow molecules smaller than 1000 daltons or less than ~1.5 nm to pass as shown in FIG. 5B. Amino acids range between 0.5–1 nm in size and as such individual amino acids are shared between cells but not macromolecules of amino acids.

Trichothecenes are extremely small at around 500 daltons ranging up to 750 daltons (or ~0.8 nm to ~1.2 nm). As such they are capable of dispersing via in the 2–4 nm spaces between cells and once internalized are capable of travel through the 1.5 nm gap junction transport system between cells. Interstitial perfusion by inhalation, particularly of rapidly internalizable and highly blood insoluble macrocyclic trichothecenes as proposed by applicant, is the first step in homogenous distribution. The second more precise step is accomplished by the gap junctions transport system, distributing the internalized trichothecenes throughout the connected organ or tissue mass, without being transported to unrelated structures or appreciably entering general circulation.

Conjugated trichothecenes are too large for traveling between cells or through gap junctions. Conjugating trichothecenes with monoclonal or polyclonal antibodies greatly increases their size. The basic structural unit of an antibody molecule consists of four polypeptide chains and contains ~1320 amino acids. Adding a single average amino acid of ~0.7 nm to a 1 nm trichothecene already exceeds 1.5 nm gap junction diameter preventing use of the gap junction transport system (and that is without provisions for linker molecules). A second amino acid already exceeds the lower limit of spacing between cells.

Preparation of Trichothecenes:

Fungi can be grown in culture and the trichothecenes extracted by centrifugal partition chromatography as described in Tani et. al. and described in other literature such as Onji et. al. (Onji, Y., Aoki, Y., Yamazoe, Y., Dohi, Y., and Moriyamam, T., 1988 *Isolation of nivalenol and fusarenon-X from pressed barley culture by centrifugal partition chromatography, Journal Liquid Chromatography,* 11:2537–2546) or Jarvis et al. (Jarvis, B. B., R. M. Eppley, and E. P. Mazzola, 1983 *Chemistry and Bioproduction of the Macrocyclic Trichothecenes,* p 20–38. In Y. Ueno, *Trichothecenes: chemical, biological, and toxicological aspects,* vol 4. Elsevier Science Publishing Inc., New York) or Sorensen et al. (Sorenson, W. G., Frazer, D. G., Jarvis, B. B., Simpson, J., and Robinson, Va., *Trichothecene Mycotoxins in Aerosolized Conidia of Stachybotrys atra,* Jun. 1987 *Applied and Environmental Microbiology,* Vol. 53 No. 6, p. 1370–1375) where *S. atra* was grown on sterile rice, autoclaved, dried, and then aerosolized by acoustic vibration and collected on glass-fiber filters and extracted with 90% aqueous methanol.

Alternatively, certain trichothecene mycotoxins can be purchased from companies such as Sigma Chemical Co. St. Louis Mo., USA or Wako Pure Chemical Industries, Ltd., Japan, or Wellcome Research Labs, Buckinghamshire, England or Boehringer-Mannheim, Manheim, West Germany.

The preferred embodiment of current invention envisions using Satratoxin H as well as other combinations of trichothecenes such as satratoxins G, H, F, roridin E, verrucarin J, and trichoverrols A and B for reasons discussed later. These trichothecenes can be obtained by growing the fungus *stachybotrys atra* on sterile rice and extracting the trichothecenes by centrifugal partition chromatography as described in Tani et. al. or having it grown on sterile rice, autoclaved, dried, and then aerosolized by acoustic vibration and collected on glass-fiber filters and extracted with 90% aqueous methanol as described by Sorensen et al.

Method of Administration:

Preferred embodiment of current invention administers trichothecenes by inhalation in their raw dry powder form through commercially available dry powder inhaler devices such as the Pulmicort Turbuhaler breath activated dry powder inhaler (Astra USA Inc., Westborough, Mass.) or Galaxo Wellcome's Diskus inhaler. However, any suitable commercially available inhaler devices, nebulizers, or any other suitable means and in combination with any suitable solution or device to facilitate inhalation, retention, or absorption by the lungs may be used. Such devices are commercially available from sources such as Self Care, Emeryville, Calif., USA and enclosed examples include the Lumiscope Ultrasonic Nebulizer, the Dura-Neb®3000 Portable compressor driven nebulizer, the PARI LC plus Nebulizer, the Omron CompAir Compressor Nebulizer System, the SpaceChamber™ aerosol spacer, and other devices.

Alternatively, therapeutics of present invention may also be administered by cigarette (either tobacco or other). Trichothecenes require temperatures of 500° F. for 30 minutes for inactivation allowing them to still be biologically active after being inhaled through a lit cigarette. The diseases considered for treatment under present invention such as COPD are primarily caused by smoking. Methods of mixing additives with tobacco are established in prior art in the tobacco industry. Measurement of effective dosages of trichothecenes inhaled per cigarette can be determined by using equipment developed in prior art for testing tar and nicotine content inhaled per cigarette or using glass fiber filters and pumps (emulating human inhalation patterns from cigarettes) and measurement of collected dosages could be performed after extraction with 90% aqueous methanol as described in Sorensen et. al. The appropriate number of cigarettes to be smoked to deliver the desired therapeutically effective dosages would then be determined.

Dose Determination:

FIGS. 1A and 1B show the hyperactive protein synthesis inhibiting dose profile of roridin A and satratoxin G, respectively. Both roridin A and satratoxin G are macrocyclic trichothecenes. By ~5 ng/ml both had inhibited almost 100% of the hyperactive protein synthesis. Both did not reduce cell viability at concentrations of 10 ng/ml or less.

Figure 2A:
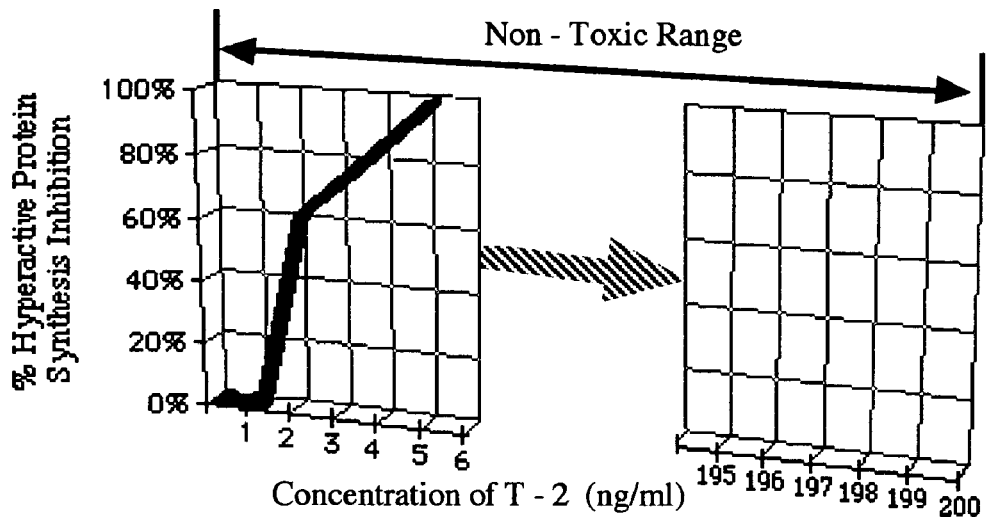
FIG. 2A shows the hyperactive protein synthesis inhibiting dose profile in human cells of T-2, a representative simple trichothecene.
Figure 2B:
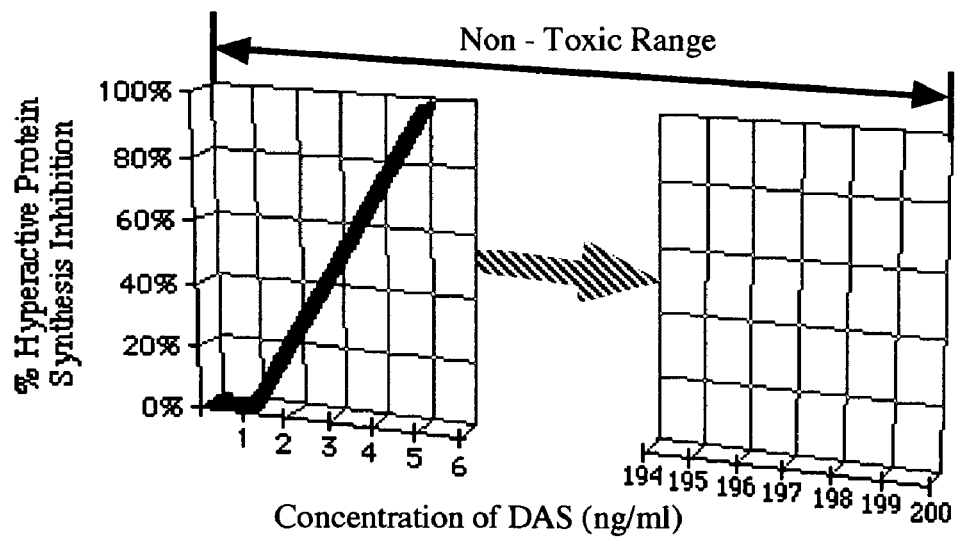
FIG. 2B shows the hyperactive protein synthesis inhibiting dose profile in human cells of DAS, a representative simple trichothecene.

FIGS. 2A and 2B show the hyperactive protein synthesis inhibiting dose profile of T-2 and DAS, respectively. Both T-2 and DAS are simple trichothecenes. By doses of 5 ng/ml both had inhibited ~99% of hyperactive protein synthesis. Neither reduced cell viability at concentrations up to 200 ng/ml.

The hyperactive protein synthesis inhibiting profiles were constructed from data collected from in vitro experiments using human epidermoid cells, virally infected with HSV-2 to induce a hyperactive state of protein synthesis, and conducted and reported by Okazaki et. al. in the attached Journal of Agricultural and Biological Chemistry articles.

Conversion of in vitro concentrations to dosages required to achieve in vivo concentrations would be performed by simple mathematical methods. As an example, if a patients has an average lung weight of ~1200 grams and one desires to achieve a 5 ng/ml concentration of Satratoxin one would need to administer ~6,000 ng of dry satratoxin (i.e. 1 gram=1 ml, 1200 gram lungs ~1200 ml, 1200 ml×5 ng/ml=6,000 ng.) by inhalation methods described above. Adjustments would be made for individual lung size differences and additional tissue mass where applicable.

Inhibitory, Cytotoxic, and Toxic doses are used in various treatment applications discussed later in the application. Using the data from the viral protein synthesis inhibiting model referenced above, dose guidelines for use in the Inhibitory, Cytotoxic, and Toxic embodiments of present invention are listed below in TABLE 1 and TABLE 2. Since no reduction in cell viability was observed at concentrations of less than 10 ng/ml for the two macrocyclic trichothecenes and 200 ng/ml for the two simple trichothecenes, TABLE 3 was constructed assuming two worst case scenarios 1) that none of the inhaled trichothecene is retained by the lungs and instead all of it finds its way to the roughly 42 liters of extracellular water outside the vasculature in the body or 2) more seriously the entire dose is accidentally injected directly into the blood stream which contains roughly 5 liters. TABLE 3 displays the maximum amount of trichothecene, in ng, that would not reduce cell viability systemically under the two scenarios. The maximum locally toxic doses for use in TABLE 2 are taken from TABLE 3.

TABLE 1

Trichothecene in Vitro Concentrations (in ng/ml)

| | Inhibitory | | | | Cytotoxic | | Toxic |
|---|---|---|---|---|---|---|---|
| | 50% | 80% | 90% | 99% | Min | Max | Lo |
| Roridin A | 1.4 | 2.0 | 3.3 | 5.0 | 6 | 10 | 11 |
| Satratoxin | 1.5 | 2.4 | 3.9 | 5.0 | 6 | 10 | 11 |
| T-2 | 1.6 | 3.5 | 4.3 | 5.0 | 6 | 200 | 201 |
| DAS | 2.3 | 4.0 | 4.5 | 5.0 | 6 | 200 | 201 |

TABLE 2

In Vivo Dose for Average 1200 Gram Lungs (in ng)

| | Inhibitory | | | | Cytotoxic | | Toxic | |
|---|---|---|---|---|---|---|---|---|
| | 50% | 80% | 90% | 99% | Min | Max | Lo | Hi |
| Roridin A | 1680 | 2400 | 3960 | 6000 | 7200 | 12000 | 13200 | 50000 |
| Satratoxin | 1800 | 2880 | 4680 | 6000 | 7200 | 12000 | 13200 | 50000 |
| T-2 | 1920 | 4200 | 5160 | 6000 | 7200 | 240000 | 241200 | 1000000 |
| DAS | 2760 | 4800 | 5400 | 6000 | 7200 | 240000 | 241200 | 1000000 |

TABLE 3

Worst Case Safe Systemic Levels (in ng)

| | Max. Non Toxic @ 42 Liters | Max. Non Toxic @ 5 Liters |
|---|---|---|
| Roridin A | 420,000 | 50,000 |
| Satratoxin | 420,000 | 50,000 |
| T-2 | 8,400,000 | 1,000,000 |
| DAS | 8,400,000 | 1,000,000 |

The above are ballpark numbers for illustrative purposes. The concentrations and doses used should not be construed as "optimal". As is customary under prior art, all dosages would be further refined and scrutinized by in vivo testing in suitable animal models or in Phase I and II clinical trials on humans as required by the FDA and the lowest concentrations suitable to achieve efficacy would likely be called "optimal". The "optimal" doses could readily be expected to be much smaller than those presented for use in inhibitory or cytotoxic treatment regimens. Likewise, toxic doses, much higher than those presented above, could likely be more efficacious yet equally safe. Locally toxic doses may also be substituted in place of cytotoxic doses in many instances. The doses presented in this application were done so to fulfill the reduction to practice requirement of this application and are not intended to imply an absolute standard or "optimal" dose but are merely some representative examples of efficacious, yet safe, embodiments of present invention.

Alternative Method of Therapeutic Dose Determination:

Although specific dose profiles for therapeutics have been discussed above, present invention can easily be extended to using various other trichothecenes as well as combinations of trichothecenes (to affect the depth of penetration of therapeutics of present invention). Accordingly, a general method for dosage determination of other trichothecenes is provided below.

Human cell lines, including human lung cell lines, are commercially available from several sources including ATCC—American Type Culture Collection, Manassas, Va., USA or ECACC—European Collection of Cell Cultures, Salisbury, Wiltshire, UK or DSMZ—German Collection of Microorganisms & Cell Cultures, Braunschweig, Germany or IZSBS—Istituto Zooprofilattico Sperimentale, Brescia, Italy or ICLC—Interlab Cell Line Collection, Genova, Italy or ECBR—European Collection for Biomedical Research, Genova, Italy or any other suitable supplier. Human lung cell lines available include both normal and malignant cell lines. As an example, LL24 is a human lung cell line available from ECACC. Examples of malignant cell lines include A-427 human lung carcinoma available from DSMZ and COR-L23 human large cell lung carcinoma available from ECACC, however any other suitable cell line from any other suitable source may be used.

To establish inhibitory, cytotoxic, toxic, and lethal concentrations human lung cell lines (both normal and malignant) would be grown in culture and exposed to various concentrations of trichothecenes by methods described in Okazaki et al. or Tani et al. where human cell lines were grown in Eagle's minimum essential medium (MEM) supplemented with 10% fetal calf serum (FCS). Trichothecenes would be dissolved in dimethyl sulfoxide at a concentration of 20 mg/ml and diluted in Eagle's MEM. Stock solutions (200 $\mu$g/ml) could be prepared, passed through a 450-nm Millipore membrane filter and stored at −20° C. until use. Tissue culture plates would be seeded with normal human lung cell lines and other culture plates would be seeded with human lung cancer cell lines. Both sets of cells would then be allowed to proliferate at 37° C. until confluent monolayers had formed. The culture plates would then be exposed to various concentrations of the trichothecenes and the number of viable cells periodically counted using trypan blue exclusion after trypsinization. A "Non Cycling Cell Response" and "Actively Cycling Cell Response" profile would then be constructed for various trichothecene concentrations under prior art methods as illustrated in HPIM Figure 86-3, pg. 528 as part of constructing a Therapeutic Index profile. Observed recovery time would serve as an indicator of intracellular inactivation time for purposes of determining periodicity of administration cycles. LD50 doses could also be determined in murine models as customary under prior art.

Safety and Efficacy by Inhalation—The Cleveland Infant Model:

The cluster of infant deaths in Cleveland (NIEHS press release and MMWR report) demonstrated, in vivo, in humans, both a usable therapeutic index of certain trichothecenes when administered by inhalation, as well as their ability to localize in lung tissue without appreciably entering general circulation.

The Cleveland infants served as a model for rapidly proliferating tissues such as cancer or other hyperproliferative conditions. The mean age of the infants was ~10 weeks old (range 4–16 weeks). At this age, the lungs of infants are growing at an accelerated rate, meaning that they are actively cycling cells. Likewise the expected effects of inhaled trichothecenes would be to result in the death of these actively cycling cells.

The control group was represented by the adults living in the same household and inhaling the same trichothecenes. The median age of the infant's mothers was 20 years (range 15–29 years). At this age, the lungs of adults are not growing at an accelerated rate and are analogous to normal tissue as defined in the context of therapeutic index dose profile determination previously discussed. Non cycling cells would not be expected die at cytotoxic dose levels of trichothecene.

Both groups were subjected (inadvertently) to airborne concentrations of trichothecenes produced naturally by the fungus *Stachybotrys atra*. Trichothecenes produced by *S. Atra* include satratoxins H, G, F, roridin E, verrucarin J, and trichoverrols A and B.

The destruction of the rapidly proliferating tissues of the infants was so severe that it resulted in the death of at least 10 infants. No health problems were reported by the adults. This indicated cytotoxic dose levels were inhaled and also demonstrated that a useful therapeutic index exists at which tissue growing at an accelerated rate in the lungs is severely damaged or destroyed and normal tissue is not affected.

This also demonstrated the safety of using trichothecenes by inhalation in adults. Even in the infants, despite the acute pulmonary hemorrhage/hemosiderosis, the inhaled trichothecenes localized in the lungs and did not enter circulation where they would have caused systemic cytotoxicity. Laboratory findings on admission showed a normal white blood cell count (median=13.8 cells/ cubic mm) in the infants. Red blood cell counts were consistent with the blood loss from the hemosiderosis. No other source of bleeding (i.e. gastrointestinal or nasopharyngeal) was identified during endoscopic evaluation.

The inhaled trichothecenes are essentially "trapped" between the lumen of the lungs on one side and the circulatory system on the other side, in which they are insoluble. In between this is the lung tissue in which they eventually internalize. The molecular basis for the "localization" of these trichothecenes has been previously disclosed in the "Internalization and Localization Attributes" section of this application. Additionally, the water insolubility of trichothecenes would facilitate their escaping elimination from the lung by the by cilia driven movement of mucus. Cephalad movement of the mucus blanket at 0.5–1 mm/minute normally removes accumulated material from the lungs in ~24 hours. Since no other source of bleeding (i.e. gastrointestinal or nasopharyngeal) was identified during endoscopic evaluation, this corroborates the inability of the trichothecenes to be appreciably removed by the cephalad movement of the mucus blanket in the lungs. Furthermore, since environmental tobacco smoke was implicated in the severity of tissue destruction (NIEHS press release) and tobacco smoke is known to inactivate (and eventually destroy) cilia in the lungs, inactivating or destroying cilia results in even further increased retention of trichothecenes in the lungs, further enhancing both localization and efficacy. Consequently, smokers and smoke damaged lungs, which are the main target of therapeutics of present invention, should benefit disproportionately over normal healthy lungs. Present invention also envisions the possibility of deliberately inactivating or destroying cilia prior to administration of trichothecenes to improve localization and efficacy.

Although there have been studies on the rates at which trichothecenes are intracellularly converted into biologically inactive apotrichothecenes, the Cleveland infant model provides a rare glimpse of how slowly macrocyclic trichothecenes are inactivated, in vivo, in the lungs, after inhalation. All infants survived the first hospitalization and were discharged without evidence of hemoptysis after a median length of stay of 10 days, indicating an inactivation time at cytotoxic doses in the ballpark of a week or so.

Safety by Inhalation-AMRIID's Aerosolized Administration Model

The safety of using trichothecenes by inhalation can be further substantiated by AMRIID's research on inhalation of aerosolized trichothecenes. The simple trichothecene T-2 was evaluated (see AMRIID Table 2). Even though trichothecenes are some of the most potent toxins by weight, when AMRIID administered T-2 in aerosolized form, T-2 came 25th out of 25 toxins tested for lethality by inhalation. AMRIID computed the LD50 (lethal dose to 50% of people) by inhalation as 1,210 $\mu$g/kg of body weight. This translates to a 84,700,000 ng dose of T-2 being inhaled by a 70 kg person to have a 50% chance of mortality. This contrasts with the 6000 ng maximum inhibitory dose (~14,116 times smaller) for T-2, or the 240,000 maximum cytotoxic dose for T-2 (353 times smaller), or the 1,000,000 maximum toxic dose (85 times smaller) as proposed by present invention in the dose determination section of this application.

REDUCTION TO PRACTICE EXAMPLES

There are ~16 million COPD patients in the United States. COPD is a group of chronic, slowly progressive, respiratory disorders and is made up of emphysema and chronic bronchitis. COPD is the fourth leading cause of death and the only one of the top 10 for which mortality rates are still rising. COPD results from persistent inflammation (particularly from smoking) and results in narrowing of both large and small airways. Airway epithelium is characterized by squamous metaplasia (abnormal transformation of epithelium into scaly cells), atrophy of ciliated cells, an hypertrophy of mucus glands (increase in bulk). The remodeled epithelium actively produces cytokines that amplify and sustain the inflammatory process. Small airway transformation also includes overproduction of smooth muscle and goblet cells, peribronchial fibrosis, edema, intraluminal mucus plugs, and CD8+ T lymphocytes and B lymphocytes comprise the primary inflammatory infiltrates.

Palliative treatments include bronchodilators, glucocorticoids, and oxygen. Curative treatments are limited to lung transplants and Lung Volume Reduction Surgery (LVRS), an operation where severely emphysematous lung tissue is resected resulting in 25% to 50% improvement in airflow. LVRS mortality ranges from 5% to 18%, requires a hospital stay from 9 to 18 days, and costs $ 33,000 to $70,000 per case.

Examples are provided to give further guidance on methods of use of compositions of present invention as discussed above. Satratoxin H is used in the examples because it is known to be highly efficacious by inhalation in its raw, dry powder form, however any suitable trichothecene could be substituted in the examples. Likewise COPD is used as a representative example of a non malignant, hyperproliferative condition, however the examples below would apply equally well to other non malignant, hyperproliferative conditions such as endometrial lung growths.

Three examples are provided, starting from lowest to highest dose levels to illustrate the underlying MOAs at each dose level and their therapeutic benefit in inhibiting the progression or reversing the overproliferation of "undesirable" cell populations such as those observed in COPD.

Example 1

Inhibitory Dose and COPD

A patient presents with early signs of COPD. The patient is a smoker that is not able or does not desire to quit smoking.

Under present invention, the patient is administered a weekly dose of around 3000 ng (or any other suitable inhibitory dose), of satratoxin H (or any other suitable trichothecene) by cigarette (or any other suitable method of inhalation).

Alternatively, for a trichothecene with a 7 day inactivation time, under present invention, the patient is administered a daily dose of around 300 ng (or any other suitable inhibitory dose) of the trichothecene by cigarette (or any other suitable method of inhalation).

After two months (or any other suitable time interval) administrations are discontinued for 2 weeks (or any other suitable time intervals), after which time the normal administration regimens are resumed.

The 3000 ng weekly inhibitory dose represents roughly 80% protein synthesis inhibition. Alternatively the 300 ng daily dose represents an eventual homeostatic dose level of around 2000 ng or roughly 50% ongoing protein synthesis inhibition.

The purpose of the inhibitory dose is two fold. First, the inhibitory dose attenuates immune mediated inflammatory responses as covered under a divisional application. Second, the inhibitory dose also A) attenuates immune mediated production of growth factors and B) disables a cell's ability to respond to any growth factors (i.e. mitogens) by preventing the hyperactive burst of of cyclin/CDK required by the cell cycle control system as previously disclosed and shown in FIG. 3 and FIG. 4.

The purpose of the periodic drug vacation is to allow for normal replacement of cells to occur.

Example 2

Cytotoxic Dose Chemodebridement

A COPD patient presents with persistent inflammation accompanied by overproliferation of smooth muscle and other undesirable cells that are reducing the patient's ability to breath.

Under present invention, the patient is administered a 10,000 ng cytotoxic dose (or any other suitable cytotoxic dose), of satratoxin H (or any other suitable trichothecene) by dry powder inhaler (or any other suitable method of inhalation). The dose is repeated monthly (or any other suitable time interval) for one or more cycles.

The purpose of the cytotoxic dose is to kill actively cycling cells. The presence of the inflammation is indicative of an immune response. The immune response is also responsible for mediating production of growth factors (i.e. mitogens) that are responsible for the growth of the undesirable cell populations. Accordingly, the undesirable cell populations are under mitogen stimulation, will be actively cycling, and will be killed by the cytotoxic affects of the trichothecene(s). Normal, non cycling cells will not be harmed. The selective targeting of undesirable cells in this manner leave the undesirable cell population smaller and smaller with each cycle.

The month between administration cycles is provided to allow for inactivation of the trichothecenes, resumption of the immune response, resumption of mitogen production, and resumption of cycling of the undesirable cells. The stage is once again set for the cytotoxic dose administration to selectively kill these undesirable cell populations. In a sense, the immune system that spawns the overproliferation of the undesirable cells is used to stimulate their growth in a manner that makes subsequent administrations of trichothecenes highly specific to these undesirable cell populations.

Example 3

Toxic Dose Chemodebridement

A lifelong smoker has severe emphysema and would like some degree of lung function restored however they cannot afford an LVRS or are scared to by the 18% mortality rate.

Under present invention they would now have a chemexfoliation/chemical debridement option instead of surgery. The patient is administered a single normal tissue toxic level dose of 50,000 ng (or any other suitable toxic, but not lethal, dose necessary to kill a desired percentage of lung cells), of satratoxin H (or any other suitable trichothecene) by dry powder inhaler (or any other suitable method of inhalation). The administration may be repeated for one or more cycles, spaced a month (or any other suitable time interval) apart.

In this example, the toxic doses are intended to eliminate a portion of the airway epithelium now characterized by squamous metaplasia (abnormal transformation of epithelium into scaly cells), eliminate a portion of the increased bulk in the mucus glands, eliminate a portion of the remodeled epithelium that now actively produces cytokines that amplify and sustain the inflammatory process, and eliminate part of the overproduced smooth muscle cells and goblet cells.

Other Examples, Applications and Embodiments

It should be noted that the above are only a few representative examples of numerous possible embodiments of present invention are nothing should be construed as limiting the scope of present invention to only the representative examples presented above. As an example, cytotoxic or toxic dose levels can be used to kill back a desired percentage of the lung cell population, and then inhibitory doses can be used the preserve these lower levels. As another example, successive cycles of cytotoxic or toxic doses can be used to reduce lung cell counts below normal population density levels to enable lung remodeling technologies or lung rejuvenating technologies to be employed in the regrowth of the tissue to normal population density levels. Lung remodeling may include combinations of growth factors that favor the growth of "desirable" cell populations or inhibitors to discourage the growth of "undesirable" cell types. Rejuvenating technologies may include substances that upregulate telomerase (which requires a cell to be cycling to result in lengthened telomeres) in order to extend the number of cell divisions left before the cell reaches senescence.

Many other variants are also possible. The representative examples may include or exclude varying "drug vacation" periods for normal cell replacement to occur or varying periods of inhibitory doses between or after cytotoxic of toxic dose administrations. The present invention also envisions the possibility of mixing the trichothecene with other compounds or substances, including combinations of trichothecenes, or substances that facilitate administration, facilitate or regulate the rate and/or depth of penetration and/or absorption of said trichothecene mycotoxins, increase efficacy of said mycotoxins, facilitate retention of trichothecene in the lung by methods such as disabling cephalad movement of the mucus blanket, provide prophylactic activity against infection, or provide any other beneficial or synergistic function. The compounds collectively described above are termed herein "pharmaceutical compositions". As an example, a combination of macrocyclic and simple trichothecenes may be used to achieve more extensive penetration (as macrocyclics internalize faster and simple trichothecenes would migrate further before internalization). As another example, antibiotics may be included as part of the "pharmaceutical composition". As another example pharmaceutical compositions may include other protein synthesis inhibitors or angiogenesis inhibitors such as squalamine or troponin. As another example pharmaceutical composition may include any inert ingredients to facilitate or enhance distribution of therapeutics by inhalation. As another example, other agents that prevent inflammation or allergic response such as mast stabilizing agents cromolyn and nedocromil may also be included as part of the pharmaceutical composition. The examples provided in the application are only some of the potential uses of therapeutics of present invention and nothing in this application is intended to limit the potential uses of therapeutics of present invention for treatment of conditions of the lungs that could benefit from chemodebridement of the lungs.

The compositions of present invention cannot be administered to infants and young children. Care would also need to be taken that patients undergoing treatment with therapeutics of present invention do not inadvertently expose infants to therapeutics of present invention.

Summary of Novelty and Utility

The unobviousness stems in part from the ability to cleanly localize certain trichothecenes in the respiratory tract by inhalation as discovered by applicant from the cluster of infant hemosiderosis cases and from biological warfare test failures. The utility is that Chemodebridement will provide a less expensive, less painful, and less deadly alternative to surgical procedures. Chemodebridement also sets the stage (i.e. is an enabling technology) for lung remodeling or lung rejuvenation technologies. Since lung cell populations can be reduced below normal population density levels, subsequent administration of growth factors or combinations of growth factors designed to stimulate regrowth of "desirable" cell populations or to inhibit "undesirable" cell populations (i.e. lung remodeling) and/or telomerase upregulating/telomere extending substances or methods (i.e. rejuvenating) will now be enabled.

References Cited:

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th edition, McGraw Hill, 1998, Fauci, Braunwald, Isselbacher, Wilson, Martin, Kasper, Hauser, Longo.

I claim:

1. A method of chemical debridement or chemexfoliation of non malignant lung tissue in humans or non human animals, comprising administration by inhalation of a composition containing therapeutically effective amounts of trichothecene or a mixture of trichothecenes.

2. The method of claim 1 wherein said trichothecene is a fragment or subunit of trichothecene which still possesses the biological activity of inhibiting protein synthesis.

3. The method of claim 1 wherein said trichothecene is a simple trichothecene.

4. The method of claim 1 wherein said trichothecene is a Type A simple trichothecene.

5. The method of claim 1 wherein said trichothecene is Diacetoxyscirpenol.

* * * * *